United States Patent [19]

Collier

[11] 4,156,943
[45] Jun. 5, 1979

[54] HIGH-STRENGTH POROUS PROSTHETIC DEVICE AND PROCESS FOR MAKING THE SAME

[76] Inventor: John P. Collier, 12 Chandler Dr., Hanover, N.H. 03755

[21] Appl. No.: 827,236

[22] Filed: Aug. 24, 1977

[51] Int. Cl.² .............................................. A61F 1/24
[52] U.S. Cl. ..................................... 3/1.9; 3/1.913; 128/92 B; 128/92 BC; 128/92 D; 128/92 CA; 75/224
[58] Field of Search .................... 3/1.91, 1.912, 1.913, 3/1.9; 128/92 C, 92 CA, 92 B, 92 BC, 92 D; 75/224; 264/69

[56] References Cited

U.S. PATENT DOCUMENTS

| 3,852,045 | 12/1975 | Wheeler et al. ................ 428/553 X |
| 3,855,638 | 12/1974 | Pilliar ............................ 128/92 C X |
| 3,893,852 | 7/1975 | Bergman et al. ...................... 75/224 |
| 3,906,550 | 9/1975 | Rostoker et al. ................. 3/1.913 X |

OTHER PUBLICATIONS

Welsh et al., "Surgical Implants," Journal of Bone and Joint Surgery, vol. 53a, No. 5, Jul. 1971, pp. 963–977, [RD 701 J86].
Collier: Master's Thesis, "Bone Ingrowth Into Dynamically Loaded Porous Coated Intermedullary Nails", Jun. 1975, Dartmouth College, Hanover, N.H.

*Primary Examiner*—Richard D. Lovering

[57] ABSTRACT

A prosthetic device composed of a porous material that is non-corrodable and non-biodegradable by body fluids. The device has interstitial interconnecting pores in the size range between about 100 and 500 micrometers and a compression strength greater than 20,000 psi.

17 Claims, 8 Drawing Figures

HIGH-STRENGTH POROUS PROSTHETIC DEVICE AND PROCESS FOR MAKING THE SAME

The present invention relates to surgically-implanted, prosthetic devices.

Attention is called to the masters and doctoral theses of the present inventor, respectively, entitled "Bone Ingrowth Into Dynamically Loaded Porous Coated Intramedullary Nails" (June 1975) and "Porous Segmental Bone Replacements" (September 1976), which theses have been deposited in the library system of Dartmouth College, Hanover, N.H. The theses are drawn upon in the text that follows and may be used to augment the present description. Attention is also called to U.S. Pat. Nos. 2,668,531; 3,314,420; 3,605,123; 3,855,638; 3,852,045; and 3,808,606, as well as a journal article entitled "Porous surface layered prosthetic devices" (Pilliar et al), *Biomedical Engineering*, April 1975 (pp. 126-131) and "Surgical Implants" (Welsh et al), *The Journal of Bone and Joint Surgery*, July 1971 (pp. 963-997).

Prosthetic devices of the type herein disclosed may be used, for example, as metal screws, plates, pins, nails and articulating joints. In this specification the greatest emphasis is placed on the use as bone implants such as articulating joints. Due to size restrictions of human long bones, it is very difficult to carry the full structural load of the human body with an endosteal metal implant without causing eventual fatigue failure of the device. Since any implant is required to resist all loads upon it and such loads may be uniform or non-uniform, depending on the particular bone location and function of the implant, the strength requirements of an ideal implant are quite great. Studies have shown that the strength of bone when loaded in a collision or impact situation can be as much as 40,000 to 50,000 psi. Studies have also shown that the static strength of human cortical bone is about 20,000 to 22,000 psi. at a strain rate of 0.001/second.

A number of design criteria are sought in the ideal segmental bone replacement implant: the implant should last the lifetime of the patient without loss of function or initiating any adverse process response; the implant should be designed to restore the normal function of the bone in which it is implanted; the implant should be capable of development for early clinical use (about three years); and the implant must be producible on a commercial scale. To satisfy the foregoing criteria, it is necessary not only that the implant support the imposed load but that the interface between the implant and the bone also withstand the load requirements. A plastic cement (polymethyl methacrylate) is often used to improve the fit between the implant and the bone, but the porous device of the present invention opens the way for other possibilities.

It is an object of the invention to provide a prosthetic device that meets the design criteria above outlined.

A further object is to provide a prosthetic device having a porous surface extending at least 1000 micrometers into the device, yet providing the high strength characteristics required.

A still further object is to provide a prosthetic device having interconnecting pores of a size which will permit bone ingrowth, at least 100 to 500 micrometers.

Another is to provide a prosthetic device whose surface is porous but which surface is, nevertheless, sufficiently smooth to meet smoothness constraints of articulating joints.

Still another object is to provide a process for fabricating a realistic device with the above characteristics.

These and still further objects are addressed hereinafter.

The foregoing objects are achieved in a prosthetic device of which a substantial fraction of the surface thereof comprises a porous material that is substantially non-corrodable and non-biodegradable by body fluids, the porous material extending from the surface of the device to a depth of at least about 200 micrometers below said surface. Large portions of the device may be made totally of porous material rather than having only a porous surface. The material comprises a plurality of small, discrete particles in the form of a compact wherein the particles are fused together at their points of contact with each other to define a plurality of connected, interstitial pores within the porous material, and the particles being of a size and appropriately positioned relatively to one another to establish an average interstitial pore size of from about 100 micrometers to about 500 micrometers within the porous material and a porosity of between 10 and 40 percent. The device is a unitary structure having strength in compression greater than 20,000 psi.

The invention is hereinafter discussed with reference to the accompanying drawing in which:

FIG. 1 shows a typical prosthetic device that may be made using present techniques;

FIG. 2 is a photomicrograph showing a small portion of the surface of a prosthetic device, greatly enlarged ($200\times$), made in accordance with the present teaching from 60 to 80 mesh Vitallium powder sintered for three minutes at 1350° C. to yield a structure having a density of 66%, a yield strength of 20,000 psi, an elastic modulus of $11 \times 10^6$ psi and an average pore size of 150 micrometers;

Figure 1:
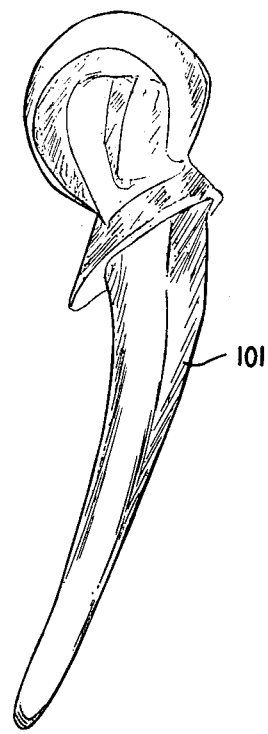
Figure 4:
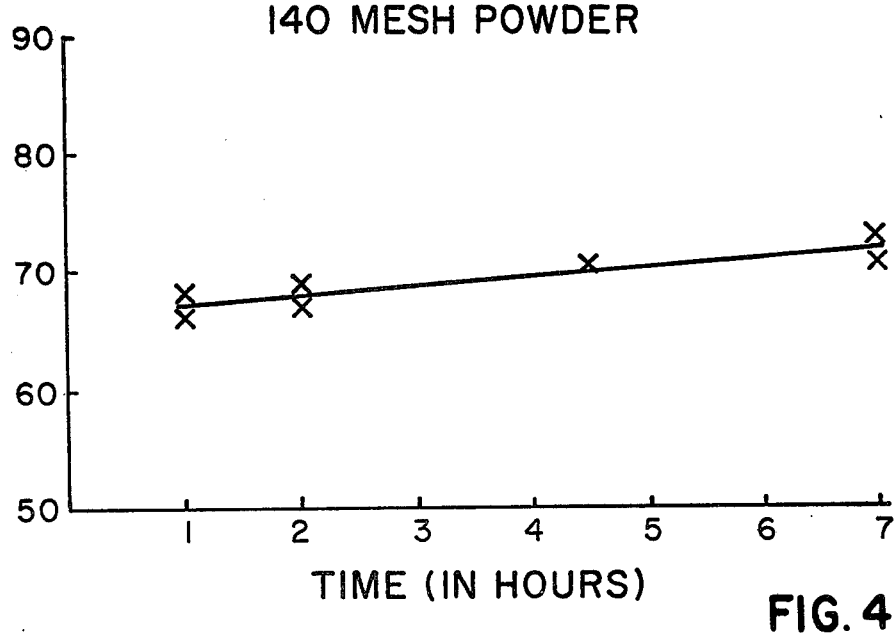
FIG. 4 is a graph of density versus time for a 140-mesh Vitallium powder sintered at 1275° C.

Before going into specifics, some preliminary general comments are in order. A very important application of the present ideas is to provide a ball joint of the type shown at 101 in FIG. 1 for hip replacements. The stem portion of the device 101 fits into a wedge-shaped cavity formed in the femur and the ball portion is received by a socket in the pelvis (the acetabulum 222). In a typical situation, polymethyl methacrylate (PMMA) bone cement is employed to improve the fit of the stem portion into the femur. It has been found that repeated loading causes the interface between the bone and the implant to fail. Usually failure begins at the interface between the plastic cement and the implant. The porous surface of the stem of the of the device 101 with pore size between about 100 and 500 micrometers (see FIGS. 2 and 3) permits the plastic cement to adhere to the stem of the device 101 to prevent such failures. Previous attempts to provide such porosity, as is noted in the doctoral thesis cited above, have resulted in devices which lacked the strength needed in such devices. The present inventor has found that both the required porosity and the required strength can be achieved by forming the prosthetic device in a process wherein powders of appropriate size (about 60 to 80 mesh) are heated to a temperature very near the melting point of the powder for a fairly short period of time. The relationships between sintering temperature and sintering time are shown in the graphs of FIGS. 4-7 for a porous material formed from Vitallium powders. It will be noted that yield strengths increase as the sintering temperature approaches the melting temperature ($\sim 1350°$ C.) of the Vitallium powder and that the final obtainable density increases as the sintering temperature increased toward the melting temperature. The sintering temperature for this process is typically within about 25° C. of the melting temperature of the powder and the sintering time is in the range between 15 minutes and one hour.

Figure 2:
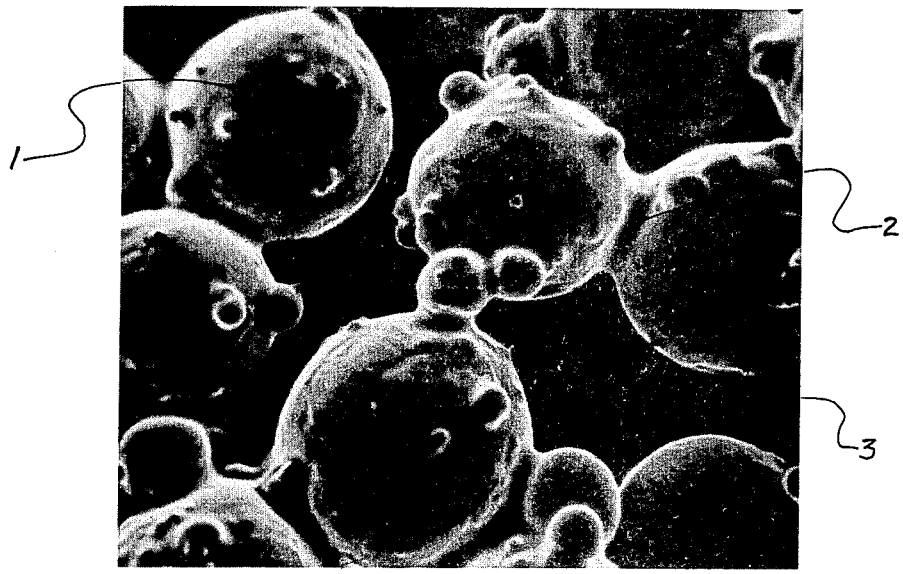
Figure 3:
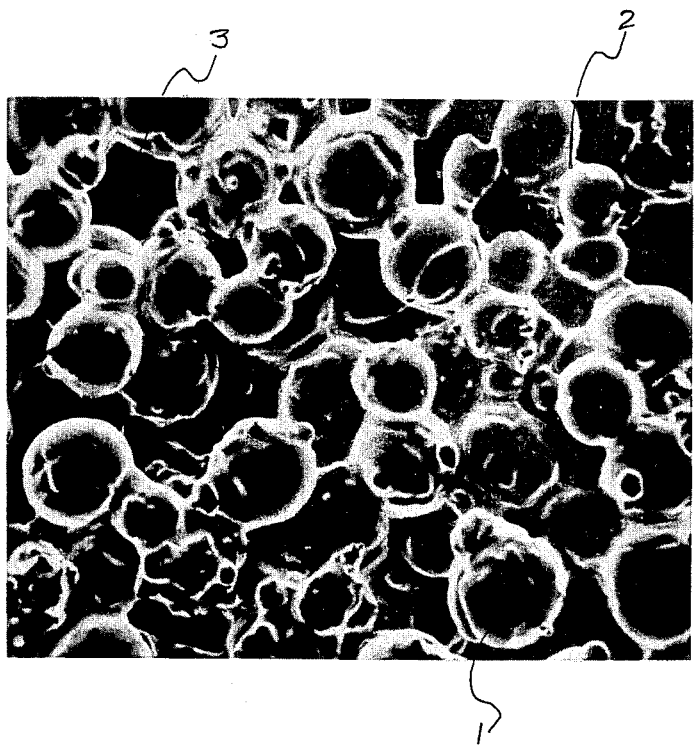
FIG. 3 is a photomicrograph ($100\times$) like that shown in FIG. 2 except that sintering was effected for seven minutes to yield a density of 85%, a yield strength of 48,000 psi, an elastic modulus of $24 \times 10^6$ psi and an average pore size of 100 micrometers.
Figure 5:
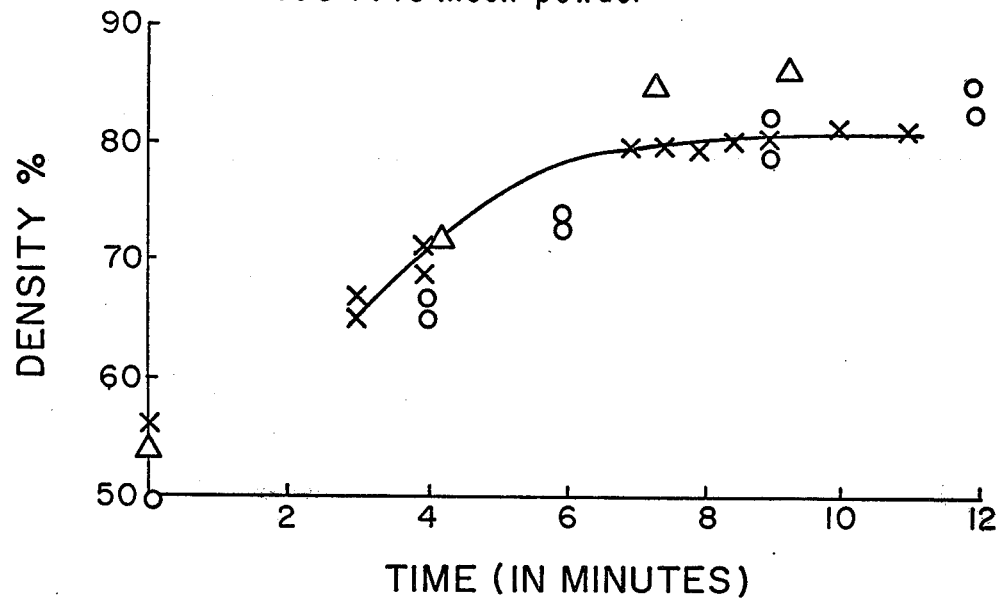
FIG. 5 is a graph, similar to the graph of FIG. 4, for different-sized powders sintered at 1350° C.
Figure 6:
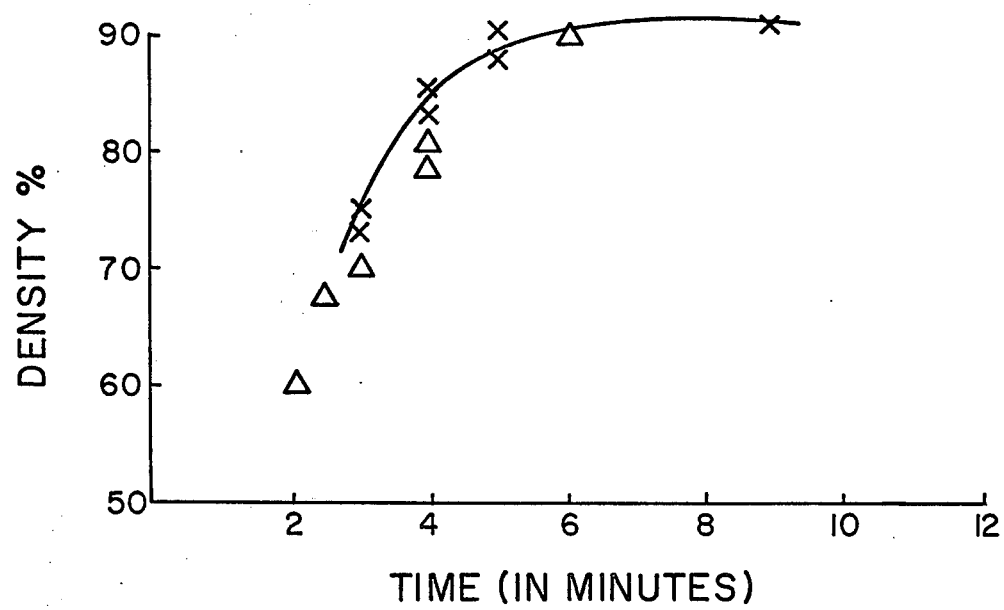
FIG. 6 is a graph, similar to the graph of FIG. 4, for different-sized powders sintered at 1375° C.
Figure 7:
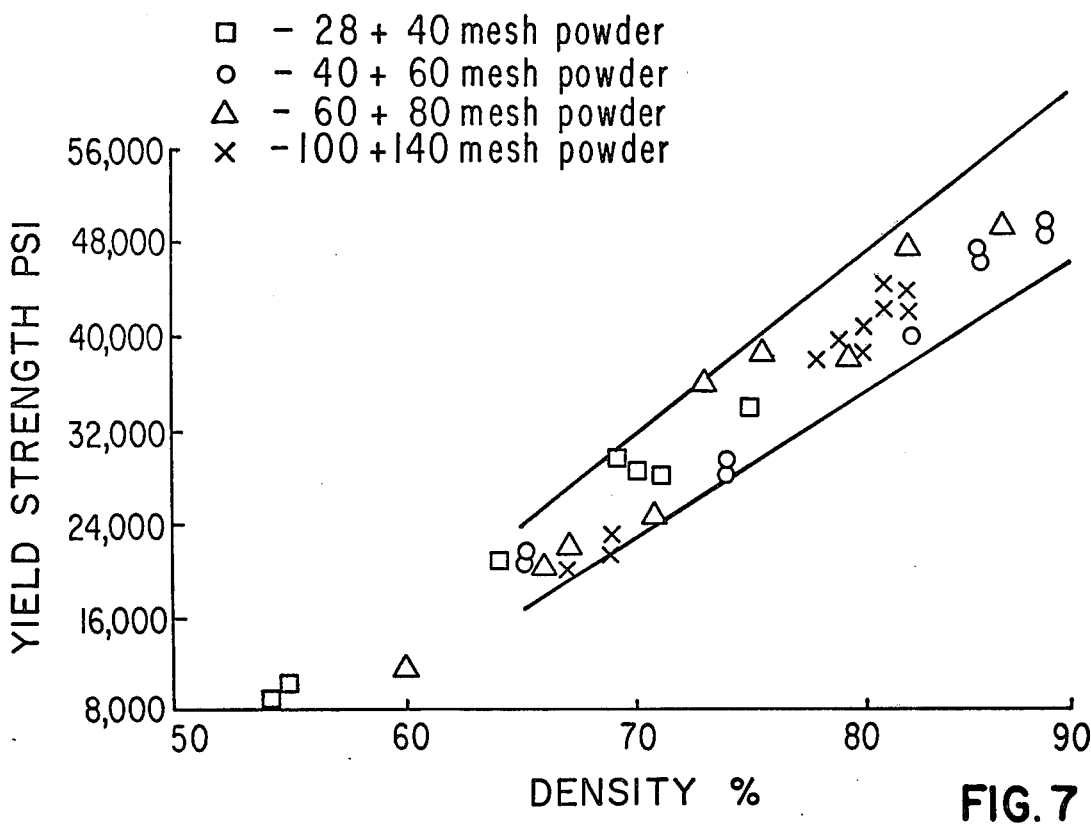
FIG. 7 is a graph of density versus yield strength for porous materials formed in accordance with the present process.
Figure 8:
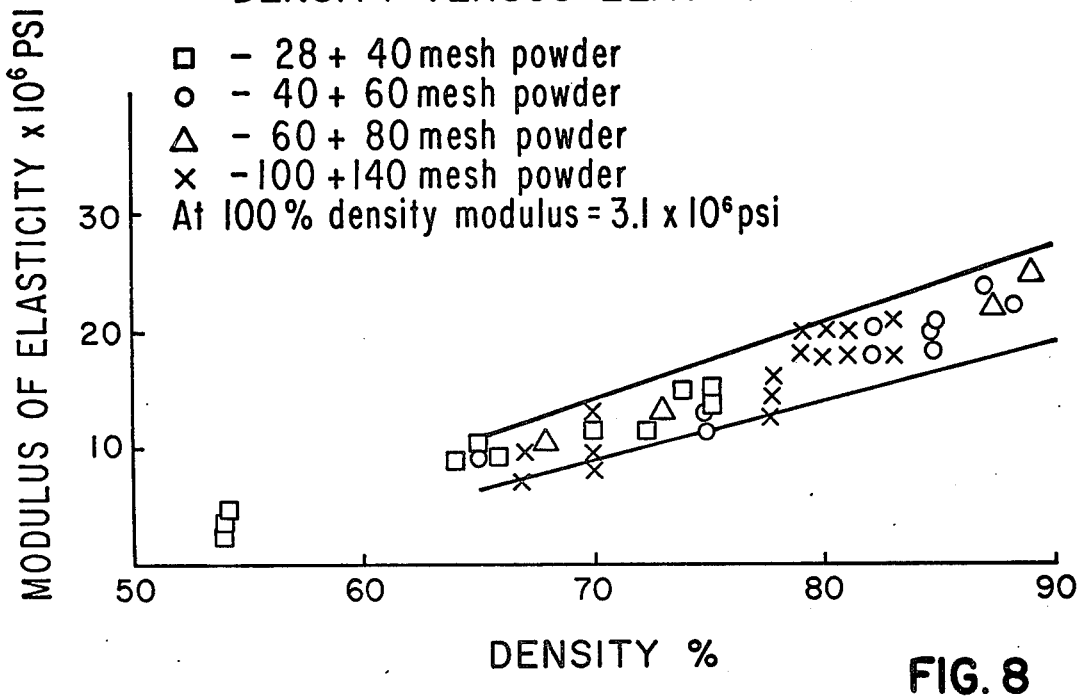
FIG. 8 is a graph of density versus elastic modulus for porous materials formed in accordance with the present process.

The resulting product, as is shown in FIG. 2 and 3, is a unitary structure wherein the original spheroidal powders are fused together at the junctions between the particles 1 such that substantially the same composition appears throughout the structure, that is, the bonds formed in the fusion process (the bonds are labeled 2 in FIGS. 2 and 3) are the same material as the powder. Further, the device thereby formed is a porous structure wherein pores 3 at and near the surface communicate or connect with pores all the way to the center of the device. In use, plastic cement will enter the pores 3 and distribute loads over a larger portion of the device than has heretofore been possible as well as permit the prosthesis to carry loads in shear and/or tension. Furthermore, it has been found that with appropriate pore size the bone will grow into the implant, again to distribute loading and permit the implant to carry loads in shear and/or tension.

The ball portion of the device 101 must slide within the receiving socket. The ball can be formed by the same sintering process herein described. A porous articulating ball will permit body fluids to pass through the interstitial pores and onto the articulation surface. Further, the pores will hold the fluid at the interface rather than permit it to be forced out of the joint by compressive loading and, hence, improve lubrication of the interface.

The processes reported in the doctoral thesis were done in an electric furnace. Briefly, the furnace consists of a tubular member to receive a device to be sintered. In practice, a rod passes through an opening in the end seal of the tubular member and the device (which may be held by a boat) is pushed into the heating chamber. After an appropriate sintering time, the device is pulled back into the tubular member. The Vitallium powders are heated to about 1325° C. and cooled afterwards to about 80° C. before being removed from the furnace. The tubular member and the heating chamber are purged with argon or some other appropriate gas (e.g., CO, $H_2$) before and during the sintering to remove free oxygen from the system, thereby preventing oxidation and permitting a solid bond (see, for example, the bonds 2 in FIGS. 2 and 3) to form between the powder spheres or particles in FIGS. 2 and 3. The graphs in FIGS. 4-8 indicate initial powder sizes, sintering temperature and sintering time. It is not believed, therefore, that further examples are needed, although further examples are, in fact, given in said doctoral thesis.

A few further matters not discussed above are contained in this paragraph and the next. For some applications, it is desirable to machine a device before it is fully sintered as the fully sintered material is difficult to machine. This can be done by forming a bio-compatible powder to the approximate shape of the desired device. Again, the size range of the initial powder is between about 60 and 80 mesh. The device thus formed is heated in a substantially oxygen-free atmosphere to a temperature near the melting point of the powder for no more than about two minutes to form a machinable compact. Then the device is machined to the desired shape and thereafter reheated (again in a substantially oxygen-free atmosphere) for a period sufficient for there to be strong bonds 2 formed at points of contact of powder particle to powder particle to provide a very dense compact having strength in compression greater than about 20,000 psi and up to, say, 50,000 psi. The pores are substantially uniformly distributed throughout the device in sufficiency to provide a porosity between 10 and 40 percent.

While Vitallium (a cobalt-based alloy also known as Haynes Stellite 21) powders are preferred, other metal biomaterials such as platinum, gold, tantalum, titanium, low carbon stainless steel, and other cobalt-based alloys may be used. Also, conceptually, ceramics, which are inert and biocompatible, may be used, but such materials now known do not have sufficient fatigue strength to be useful when employed in a porous structure.

Further modifications of the invention herein disclosed will occur to persons skilled in the art and all such modifications are deemed to be within the scope of the invention as defined by the appended claims.

What is claimed is:

1. A prosthetic device composed substantially entirely of a porous metallic material that is substantially non-corrodable and non-degradable by body fluids, said porous material comprising a plurality of particles of said metallic material fused together at points of contact with each other to define a plurality of connected, interstitial pores distributed throughout the porous metallic material, the average interstitial pore size of said material being from about 100 micrometers to about 500 micrometers, the porosity of the material being between 10 and 40 percent, and the compression strength of the material being at least about 20,000 psi, said device being formed by the process of heating a metallic powder in a non-oxidizing environment to a temperature within about 25° C. of its melting point for a period of from a few minutes to about one hour.

2. A prosthetic device in accordance with claim 1, wherein the device is a bone implant.

3. A prosthetic device in accordance with claim 1, wherein the particle size of the metallic powder is about 60 to 80 mesh.

4. A prosthetic device in accordance with claim 1, wherein the particle size of the metallic powder is from +100 to −40 mesh.

5. A prosthetic device in accordance with claim 1, wherein the metallic powder is Vitallium.

6. A prosthetic device in accordance with claim 1, wherein the material has a compression strength of about 50,000 psi.

7. A prosthetic device in accordance with claim 1, wherein the material has a yield strength of about 48,000 psi.

8. A method of making a prosthetic device composed substantially entirely of a porous metallic material that is substantially non-corrodable and non-degradable by body fluids, comprising molding a metallic powder to a shape of the device, heating the powder in a non-oxidizing environment to a temperature within about 25° C. of its melting point for a period of from a few minutes to about one hour so as to fuse particles of the powder together at points of contact with each other to form a porous metallic material having a plurality of connected, interstitial pores distributed throughout the material with average interstitial pore size of from about 100 micrometers to about 500 micrometers and with porosity between 10 and 40 percent, and having compression strength of at least about 20,000 psi.

9. A method in accordance with claim 8, wherein the heating is effected at about atmospheric pressure.

10. A method in accordance with claim 8, wherein the particle size range of the powder is about 60 to 80 mesh.

11. A method in accordance with claim 8, wherein the particle size range of the powder is about +100 to −40 mesh.

12. A method in accordance with claim 8, wherein the molded powder is vibrated prior to heating the same to effect mechanical compaction.

13. A method in accordance with claim 8, wherein the molded powder is first heated to a temperature within about 25° C. of its melting point for no more than about 2 minutes to form a machinable compact, is then cooled and machined to produce required features, and is then reheated to a temperature within about 25° C. of the melting point of the powder.

14. A method in accordance with claim 8, wherein the material is Vitallium.

15. A method in accordance with claim 14, wherein the temperature is about 1325° C.

16. A method in accordance with claim 8, wherein the period is from 3 to 7 minutes.

17. A method in accordance with claim 8, wherein the period is at least 15 minutes.

* * * * *